United States Patent [19]

Martin

[11] 4,353,736
[45] Oct. 12, 1982

[54] METHOD OF SELECTIVELY CONTROLLING WEEDS AND HERBICIDAL DIPHENYL ETHER OXIME DERIVATIVES

[75] Inventor: Henry Martin, Allschwil, Switzerland

[73] Assignee: Ciba-Geigy Corporation, Ardsley, N.Y.

[21] Appl. No.: 229,246

[22] Filed: Jan. 28, 1981

Related U.S. Application Data

[63] Continuation-in-part of Ser. No. 112,767, Jan. 17, 1980, abandoned, which is a continuation of Ser. No. 938,544, Aug. 31, 1978, abandoned.

[51] Int. Cl.³ .................... A01N 37/34; C07C 121/60
[52] U.S. Cl. .................................. 71/105; 260/465 D
[58] Field of Search ...................... 71/105; 260/465 D

[56] References Cited

U.S. PATENT DOCUMENTS

| | | | |
|---|---|---|---|
| 3,483,246 | 12/1969 | Kaufman | 71/105 X |
| 3,896,155 | 7/1975 | Hamprecht et al. | 71/105 X |
| 4,070,389 | 1/1978 | Martin | 71/105 X |

*Primary Examiner*—Catherine L. Mills
*Attorney, Agent, or Firm*—Frederick H. Rabin

[57] ABSTRACT

The present invention provides a method of selectively controlling weeds in crops of cultivated plants by the pre-emergent and preferably post-emergent method of application, the herbicidal composition employed therefore and its active components (active substances).

The novel active substances employed in the method and in the composition are diphenyl ether oxime derivatives of the formula

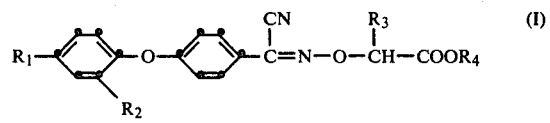

wherein
$R_1$ is chlorine or a trifluoromethyl group,
$R_2$ is hydrogen or chlorine,
$R_3$ is hydrogen or a methyl group and
$R_4$ is a $C_3$–$C_6$-alkyl or a $C_3$–$C_6$ alkenyl group.

14 Claims, No Drawings

METHOD OF SELECTIVELY CONTROLLING WEEDS AND HERBICIDAL DIPHENYL ETHER OXIME DERIVATIVES

CROSS REFERENCE TO RELATED APPLICATIONS

This is a continuation-in-part of application Ser. No. 112,767 filed on Jan. 17, 1980, now abandoned, which in turn is a continuation of Ser. No. 938,544 filed on Aug. 31, 1978, abandoned.

The present invention provides a method of selectively controlling weeds at a locus, which comprises applying to said locus certain oxime esters of the diphenyl ether series as active components, and a herbicidal composition containing novel active compounds of this series.

The invention also provides a class of novel active compounds.

Although most of the active compounds employed in the method of the invention have not yet been described in the literature, some of them form the subject matter of earlier patent applications for other fields of use.

The method according to the invention, i.e. a method of selectively controlling weeds in crops of cultivated plants, such as cereals, maize, rice and soja, comprises treating sown cultivated areas in pre-emergent application, or preferably weed infested crops of the said cultivated plants in post-emergent application, with an effective amount, not exceeding 6 kg of active ingredient per hectare of treated crop area, of a composition which contains as the said active ingredient a diphenyl ether oxime derivative of the formula I

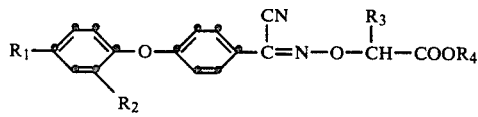

wherein
- $R_1$ is chlorine or preferably the trifluoromethyl group,
- $R_2$ is hydrogen or preferably chlorine,
- $R_3$ is hydrogen or preferably the methyl group and
- $R_4$ is a straight-chain or branched $C_1$–$C_6$ alkyl or a $C_3$–$C_6$ alkenyl group.

Preferred radicals $R_4$ are $C_1$–$C_6$ alkyl groups, such as methyl, ethyl, n-propyl, isopropyl, the four isomeric butyl groups or branched or unbranched pentyl- and hexyl groups. The methyl group and the different butyl groups, e.g. isobutyl are the most preferred. Among the lower esters, the compound wherein $R_1$ is $CF_3$, $R_2$ is chlorine, $R_3$ and $R_4$ are methyl, is an outstanding good herbicidally active ingredient.

The novel herbicidal active compounds (active substances) of the present invention are higher oxime esters of substituted diphenyl ether derivatives which contain a cyano group and have the formula Ia

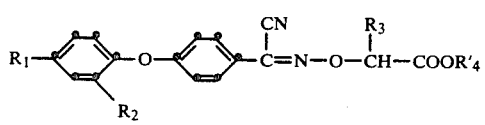

wherein
- $R_1$ is chlorine or a trifluoromethyl group,
- $R_2$ is hydrogen or chlorine,
- $R_3$ is hydrogen or a methyl group and
- $R_4'$ is a $C_3$–$C_6$-alkyl or a $C_3$–$C_6$ alkenyl group.

The term "alkyl" by itself or as moiety of a substituent comprises branched or unbranched $C_3$–$C_6$ alkyl groups, for example: n-propyl, iso-propyl, n-butyl, sec-butyl, iso-butyl, tert-butyl, as well as the higher homologues amyl, iso-amyl or hexyl together with the isomers thereof. Alkenyl radicals are aliphatic radicals containing preferably one or also two double bonds (alkadienyls) and not more than 6, preferably 4, carbon atoms.

Preferred active compounds of the formula Ia are those in which $R_1$ represents a trifluormethyl group, $R_2$ is chlorine, $R_3$ is hydrogen or especially a methyl group and $R_4'$ is a $C_3$–$C_6$ alkyl group.

Preferred compounds amongst these are compounds of the formula Ia, wherein $R_4'$ represents a straight or branched butyl group, for instance isobutyl.

Particularly preferred compounds of this last-mentioned group are those compounds of the formula Ia, wherein $R_3$ is methyl and $R_4'$ represents iso-propyl, n-butyl, sec-butyl, iso-butyl or tert-butyl.

Another preferred range of active herbicides of the formula Ia is that, wherein $R_1$ represents trifluoromethyl, $R_2$ represents chlorine and $R_4'$ represents a $C_3$–$C_6$ alkenyl group.

Particularly preferred within this scope is that compound, wherein $R_4'$ represents a 2-methyl-2-propenyl group (methallyl).

The compounds of the formulae I and Ia are obtained by methods which are in themselves known.

The following most important process may be mentioned:

A substituted diphenyl ether of the formula

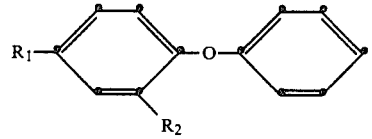

is reacted with hydrochloric acid and formaldehyde to give the corresponding phenoxybenzyl chloride of the formula

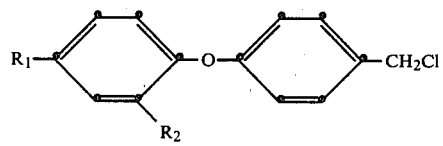

and this compound is converted with KCN into the corresponding cyanomethyl derivative (—CH$_2$CN). Reaction of this latter with, for example, $C_5H_{11}$—O—N=O in the presence of sodium ethylate (NaOC$_2$H$_5$) yields an oxime salt of the formula

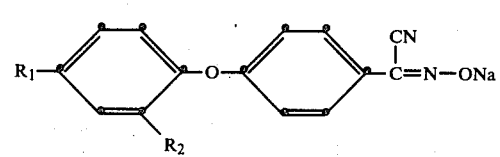

which is then converted with a compound

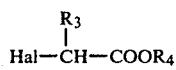

into an end product of the formula I.

These reactions are carried out at temperatures between 0° and 150° C. and in suitable solvents, such as acetone, methyl ethyl ketone, acetonitrile, dimethyl formamide, dimethyl sulfoxide etc.

These and other condensation reactions of α-oximino compounds and the alkali metal salts thereof with similar reactants are described in "Organic Reactions", 1953, Vol. 7, pp. 343 and 373.

Oximes always exist in two stereoisomeric forms, the syn-form and anti-form. Throughout this specification, both stereoisomeric forms shall be understood as existing individually and as mixtures in any ratio.

The following Examples describe the preparation of a number of active compounds (active substances) of the formulae I and Ia.

EXAMPLE 1

(a) 30 g of 2-chloro-4-trifluoromethyldiphenyl ether, 7.1 g of paraformaldehyde, 13 ml of 84% phosphoric acid, 33 ml of conc. hydrochloric acid and 70 ml of glacial acetic acid are heated to 85° C. in a three-necked flask equipped with stirrer and reflux cooler. The mixture is heated until all the para-formaldehyde has been consumed. After cooling, the reaction mixture is poured into ice-water and extracted with toluene. The toluene solution is washed firstly with water and then with 10% aqueous sodium carbonate solution, dried over sodium sulfate, and concentrated. Vacuum distillation of the residue yields 28.8 g of the product of the formula

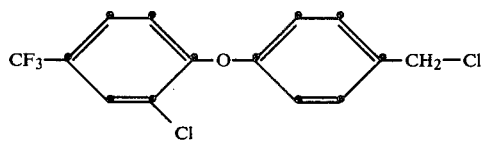

Boiling point: 108° C./0.005 mm.

(b) 9 g of the 4-(2'-chloro-4'-trifluoromethylphenoxy)-benzyl chloride obtained in (a), 2 g of finely powdered sodium cyanide, a trace of sodium iodide and 30 ml of acetone are refluxed for 24 hours in a three-necked flask. The reaction mixture is cooled and precipitated sodium chloride is removed by filtration. The filtrate is washed with acetone and the acetonic solution is concentrated in vacuo. The residue is subjected to vacuum distillation, affording 7.7 g of the benzyl cyanide of the formula

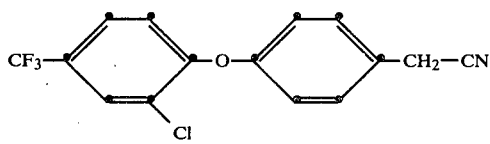

Boiling point: 156° C./0.01 mm.

(c) 2.3 g of sodium are dissolved in 70 ml of alcohol under nitrogen and with stirring in a three-necked flask and the solution is cooled to 0° C. At this temperature, there are first added dropwise 31.2 g of 4-(2'-chloro-4'-trifluoromethylphenoxy)-benzyl cyanide in the course of one hour and then 13.4 ml of isopentyl nitrite ($C_5H_{11}ONO$), whereupon the solution turns yellowish red in colour. The reaction mixture is stirred for 24 hours at room temperature and then 200 ml of ether are added. The precipitate is collected by filtration and washed with ether, affording 9.7 g of the oxime salt of the formula

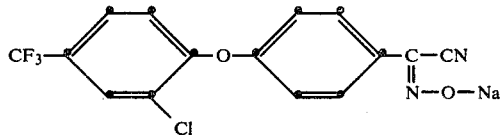

Melting point: 250° C.

(d) 9.5 g (0.026 mole) of the above sodium 4-(2'-chloro-4'trifluoromethylphenoxy)-phenylglyoxylonitrile-2-oxime are suspended in 50 ml of ethyl methyl ketone in a 100 ml sulfonating flask. Then 3.1 ml of methyl 2-bromopropionate are added dropwise, whereupon the temperature rises to 31° C. The reaction mixture is further stirred for 2 hours at 40° C., then cooled to 20° C. Sodium salt is removed by filtration and the filtrate concentrated in vacuo, affording 10.6 g of the end product of the formula

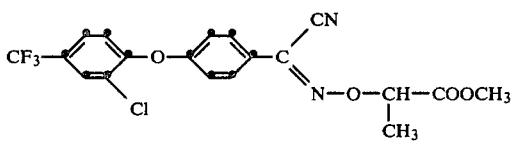

as a slightly yellowish oil; $n_D^{21} = 1.5402$.

EXAMPLE 2

18.1 g (0.05 mole) of sodium 4-(2'-chloro-4'-trifluoromethylphenoxy)-phenylglyoxylonitrile-2-oxime are suspended in 70 ml of dimethylformamide in a 250 ml sulfonating flask. Then 10.5 g iso-butyl 2-bromopropionate are added dropwise, whereupon the temperature rises to 35° C. The reaction mixture is further stirred over night at room temperature, then cooled to 20° C. and subsequently allowed to flow into about 2 liters of water. The precipitated oil is extracted with ethyl acetate, then the organic phase is washed with water and dried with sodium sulfate. The sodium sulfate is removed by filtration and the solvent is distilled off, affording 17.1 g of the end product of the formula

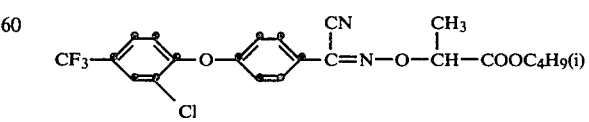

as a slightly yellowish oil; $n_D^{24} = 1.5281$.

Table 1 lists the above compounds and further novel compounds which are obtained in analogous manner.

TABLE 1

Compounds of the structure

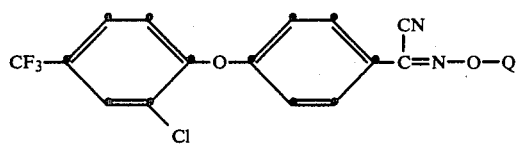

| Compound | Q | Physical constants ($n_D$, m.p. in °C.) |
|---|---|---|
| 1 | —CH(CH₃)—COOC₃H₇(n) | $n_D^{24} = 1.5328$ |
| 2 | —CH(CH₃)—COOC₃H₇(i) | $n_D^{24} = 1.5314$ |
| 3 | —CH(CH₃)—COOC₄H₉(n) | $n_D^{24} = 1.5281$ |
| 4 | —CH(CH₃)—COOC₄H₉(sec) | $n_D^{24} = 1.5298$ |
| 5 | —CH(CH₃)—COOC₄H₉(iso) | $n_D^{24} = 1.5281$ (Example 2) |
| 6 | —CH(CH₃)—COOC₄H₉(t) | $n_D^{30} = 1.5254$ |
| 7 | —CH₂—COOC₄H₉(t) | $n_D^{30} = 1.5252$ |
| 8 | —CH(CH₃)—COOC₅H₁₁(n) | $n_D^{24} = 1.5245$ |
| 9 | —CH(CH₃)—COOCH₂—C₄H₉(t) | $n_D^{30} = 1.5218$ |
| 10 | —CH(CH₃)—COO—CH(CH₃)—CHCH₃ | $n_D^{30} = 1.5235$ |
| 11 | —CH(CH₃)—COO—CH₂—CH(CH₃)C₂H₅ | $n_D^{27} = 1.5148$ |
| 12 | —CH(CH₃)—COO—CH(C₂H₅)—C₂H₅ | $n_D^{30} = 1.5229$ |
| 13 | —CH(CH₃)—COO—CH₂—CH(C₂H₅)—C₂H₅ | $n_D^{30} = 1.5230$ |
| 14 | —CH(CH₃)—COOCH₂—CH(CH₃)—C₃H₇(n) | $n_D^{30} = 1.5214$ |
| 15 | —CH(CH₃)—COOCH₂—CH=CH₂ | |
| 16 | —CH(CH₃)—COOCH₂—C(CH₃)=CH₂ | oil |
| 17 | —CH(CH₃)—COOCH₂—CH=CH—CH₃ | |

TABLE 1-continued

Compounds of the structure

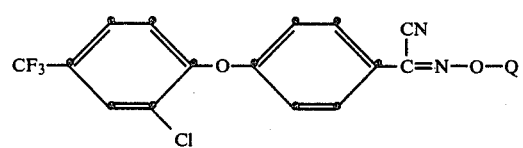

| Compound | Q | Physical constants ($n_D$, m.p. in °C.) |
|---|---|---|
| 18 | —CH(CH₃)—COOCH₃ | $n_D^{31} = 1.5402$ (Example 1) |

The active substances of the formula I are stable compounds which are soluble in conventional organic solvents, such as alcohols, ethers, ketones, dimethyl formamide, dimethyl sulfoxide etc.

The active substances of the formula I can be used by themselves, but more advantageously together with suitable carriers and/or other adjuvants, in the form of herbicidal compositions for controlling weeds.

Surprisingly, already in rates of application of less than 6 kg/hectare e.g. 0.5 to 4 kg/hectare, the active substances and compositions which contain them have pronounced action especially on dicotyledonous weeds, such as Sida, Sesbania, Amaranthus, Sinapis, Ipomoea, Galium, Pastinak, Rumex, Matricaria, Chrysanthemum, Abutilon, Solanum etc. However, when employed in higher rates of application of at least 2 to 4 kg/hectare, a number of the active compounds act on monocotyledonous weeds, such as Digitaria, Setaria and Echinochloa, whilst monocotyledonous cultivated plants, such as barley, wheat, maize, oats and rice, and furthermore the dicotyledonous leguminous plants, such as soybeans remain virtually undamaged at lower rates of application and suffer only minor damage at higher rates.

With many of these active compounds, for example with compounds Nos. 1, 2, 5, 8, 9 and 18, it has been possible to obtain good practical results in selectively controlling in particular dicotyledonous weeds in creals, maize, rice and soybeans.

The active substances and compositions containing them can be employed as contact herbicides in pre-emergent application to sown cultivated areas, but preferably in post-emergent application to weed-infested crops of cultivated plants.

The compositions of the present invention are obtained in known manner by intimately mixing and grinding active substances of the general formula I with suitable carriers and/or dispersants, with or without the addition of antifoam agents, wetting agents, dispersants and/or solvents which are inert to the active substances. The active substances can be processed to the following formulations:

solid formulations: dust, tracking powders, granules (coated granules, impregnated granules and homogeneous granules),
active substance concentrates which are dispersible in water: wettable powders, pastes, emulsions, emulsifiable concentrates;
liquid formulations: solutions.

The active substance concentrations in the compositions of the invention are between 1 and 80 percent by weight. As circumstances may require, the active substances can also be applied in low concentrations of about 0.05 to 1 percent by weight.

The following Examples illustrate in more detail the preparation of solid and liquid formulation of the compositions of the invention. The parts are by weight.

Granules

The following ingredients are used to prepare 5% granules:

5 parts of one of the active substances of the formula I,
0.25 parts of epoxidised vegetable oil
0.25 parts of cetyl polyglycol ether,
3.50 parts of polyethylene glycol,
91 parts of kaolin (particle size 0.3–0.8 mm).

The active substance is mixed with epoxidised vegetable oil and dissolved with 6 parts of acetone, and the polyethylene glycol and cetyl polyglycol ether are then added. The resultant solution is sprayed on kaolin and subsequently evaporated in vacuo.

Wettable Powder

The following constituents are used to prepare (a) a 70% and
(b) a 10% wettable powder:

(a)

70 parts of compound No. 5 of table 1,
5 parts of sodium dibutylnaphthalene sulphate,
3 parts of naphthalenesulphonic acid/phenolsulphonic acid/formaldehyde condensate (3:2:1),
10 parts of kaolin,
12 parts of Champagne chalk;

(b)

10 parts of compound No. 1 of table 1,
3 parts of a mixture of the sodium salts of saturated fatty alcohol sulphates,
5 parts of naphthalenesulphonic acid/formaldehyde condensate,
82 parts of kaolin.

The respective active substance is applied to the corresponding carriers (kaolin and chalk) and then these are mixed and ground, to yield wettable powders of excellent wettability and suspension powder. By diluting these wettable powders with water it is possible to obtain suspensions containing 0.1 to 80% of active substance. These suspensions are suitable for controlling weeds in cultivations of plants.

Paste

The following substances are used to prepare a 45% paste:

45 parts of an active substance of the formula I, e.g. compound No. 9 of table 1,
5 parts of sodium aluminium silicate,
14 parts of cetyl polyglycol ether with 8 moles of ethylene oxide,
1 part of oleyl polyglycol ether with 5 moles of ethylene oxide,
2 parts of spindle oil,
10 parts of polyethylene glycol,
23 parts of water.

The active substance is intimately mixed with the additives in appropriate devices and ground. A paste is obtained from which, by dilution with water, it is possible to manufacture suspensions of the desired concentration of active substance.

Emulsifiable Concentrate

The following ingredients are mixed to prepare 25% emulsifiable concentrate:

25 parts of an active substance of the formula I,
5 parts of a mixture of nonylphenolpolyoxyethylene and calcium dodecylbenzenesulphonate,
15 parts of cyclohexanone,
55 parts of xylene.

This concentrate can be diluted with water to give emulsions in suitable concentrations of e.g. 0.1 to 10%. Such emulsions are suitable for controlling weeds in cultivations of plants.

The following test methods were employed to establish the usefullness of the compounds of the formula I as herbicides (pre- and post-emergent).

Pre-emergent herbicidal action (germination inhibition)

In a greenhouse, immediately after sowing the test plants in seed dishes the surface of the soil is treated with an aqueous suspension of the active substances obtained from a 25% emulsifiable concentrate or from a 25% wettable powder with active substances which, because of insufficient solubility, cannot be prepared as emulsifiable concentrate. Four different concentration series were used, corresponding to 4, 2, 1 and 0.5 kg of active substance per hectare respectively. The seed dishes are kept in the greenhouse at 22°–25° C. and 50 to 70% relative humidity. The test is evaluated 3 weeks later according to the following rating:

1 = plants have not germinated or are totally withered
2–3 = very strong action
4–6 = medium action
7–8 = insignificant action
9 = no action (as untreated control)
— = plant in corresponding active substance concentration not tested.

Post-emergent herbicidal action (Contact herbicide)

A large number (at least 7) of weeds and cultivated plants, both mono- and dicotyledonous, were sprayed after emergence in the 4- to 6-leaf stage with an aqueous active substance dispersion in rates of 0.5 and 1.0 kg of active substance per hectare and kept at 24°–26° C. and 45–60% relative humidity. The test was evaluated 15 days after treatment in accordance with the same rating. The results are summarized in the following table no 2.

TABLE 2

| | | Post-emergence herbicidal action (contact herbicide) | | | | | | | | | | | |
|---|---|---|---|---|---|---|---|---|---|---|---|---|---|
| | Compound | 1 | | 2 | | 5 | | 8 | | 9 | | 18 | |
| | amounts in grams/ha: | 1000 | 500 | 1000 | 500 | 1000 | 500 | 1000 | 500 | 1000 | 500 | 1000 | 500 |
| culture | plants tested | | | | | | | | | | | | |
| crops | barley (Hordeum) | 8 | 8 | 7 | 8 | 8 | 9 | 8 | 9 | 8 | 9 | 8 | 8 |
| | wheat (Triticum) | 7 | 8 | 8 | 8 | 8 | 8 | 8 | 8 | 9 | 9 | 8 | 9 |
| | maize (Zea) | 7 | 8 | 7 | 8 | 9 | 9 | 9 | 9 | 9 | 9 | 8 | 9 |
| | rice (Oryza) | 8 | 9 | 8 | 9 | 8 | 8 | 9 | 9 | 9 | 9 | 9 | 9 |
| | soybeans (Glycine) | 5 | 7 | 6 | 7 | 8 | 9 | 7 | 9 | 7 | 8 | 6 | 7 |
| dicotyledonous | Abutilon | 1 | 3 | 1 | 1 | 1 | 1 | 1 | 1 | 1 | 3 | 2 | 3 |
| weeds | *Sida spinosa* | 3 | 3 | 3 | 3 | 2 | 3 | 3 | 3 | 4 | 5 | 2 | 3 |
| | Portulaca sp. | 2 | 4 | 1 | 1 | 1 | 1 | 1 | 2 | 1 | 2 | 1 | 2 |
| | *Sesbania ex.* | 1 | 1 | 1 | 2 | 1 | 1 | 1 | 1 | 1 | 3 | 1 | 1 |
| | *Amaranthus ret.* | 1 | 1 | 1 | 1 | 1 | 1 | 1 | 1 | 1 | 1 | 1 | 1 |
| | *Kochia scoparia* | 1 | 1 | 1 | 2 | 2 | 3 | 6 | 7 | 7 | 8 | 2 | 3 |
| | *Solanum nigrum* | 1 | 2 | 1 | 1 | 1 | 1 | 3 | 3 | 1 | 1 | 1 | 1 |
| | Ipomoea | 1 | 1 | 1 | 1 | 1 | 2 | 1 | 2 | 2 | 3 | 1 | 1 |
| | Sinapis | 1 | 1 | 1 | 1 | 1 | 1 | 1 | 1 | 1 | 2 | 1 | 1 |
| | Stellaria | 1 | 1 | 1 | 1 | 2 | 3 | 6 | 7 | 9 | 9 | 2 | 2 |
| | *Chrysanthe. leuc.* | 2 | 1 | 1 | 1 | 1 | 1 | 1 | 1 | 2 | 2 | 1 | 2 |
| | *Galium aparine* | 1 | 1 | 2 | 2 | 2 | 2 | 1 | 2 | 2 | 3 | 1 | 2 |

What we claim is:

1. A method of selectively controlling weeds in crops of barley, wheat, maize, rice and oats, which comprises treating sown cultivated areas in pre-emergent application, or weed-infested crops of cultivated plants in post-emergent application, with an effective amount, not exceeding 6 kg of active ingredient per hectare of treated crop area, of a diphenyl ether oxime derivative of the formula I

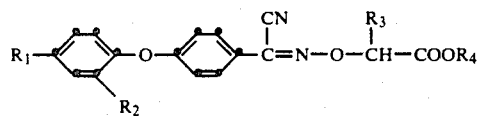

wherein
$R_1$ is chlorine or a trifluoromethyl group,
$R_2$ is hydrogen or chlorine,
$R_3$ is hydrogen or a methyl group and
$R_4$ is a $C_1$–$C_6$-alkyl or a $C_3$–$C_6$ alkenyl group.

2. A method according to claim 1 in which the compound is of the formula

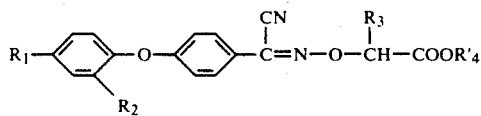

wherein
$R_1$ is chlorine or the trifluoromethyl group,
$R_2$ is hydrogen or chlorine,
$R_3$ is hydrogen or the methyl group and
$R_4$ is a $C_3$–$C_6$ alkyl or a $C_3$–$C_6$ alkenyl group.

3. A method according to claim 1 in which the compound is

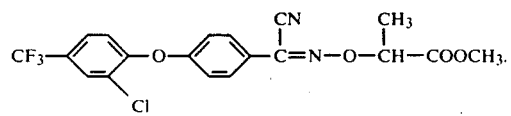

4. A compound of the formula

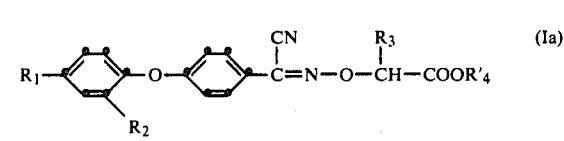

wherein
$R_1$ is chlorine or the trifluoromethyl group,
$R_2$ is hydrogen or chlorine,
$R_3$ is hydrogen or the methyl group and
$R_4'$ is a $C_3$–$C_6$-alkyl or a $C_3$–$C_6$ alkenyl group.

5. A compound according to claim 4 wherein $R_1$ represents the trifluoromethyl group, $R_2$ is chlorine and $R_4'$ is a $C_3$–$C_6$ alkyl group.

6. A compound according to claim 5 wherein $R_4'$ represents a straight or branched butyl group.

7. The compound according to claim 6, of the formula

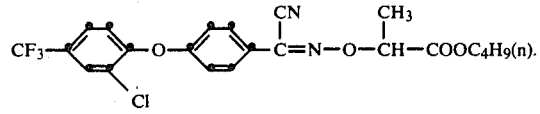

8. The compound according to claim 6, of the formula

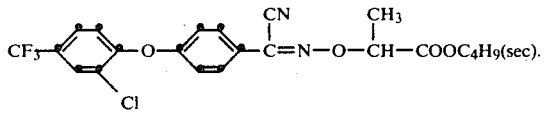

9. The compound according to claim 6, of the formula

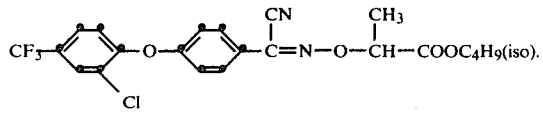

10. The compound according to claim 6, of the formula

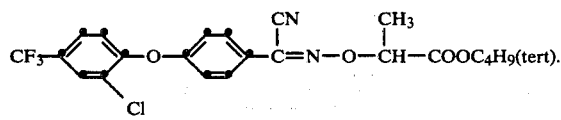
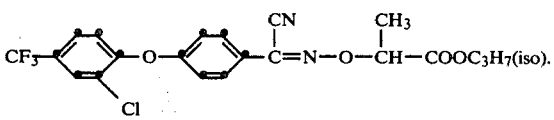

11. The compound according to claim 5, of the formula

12. A compound according to claim 4 wherein $R_1$ represents trifluoromethyl, $R_2$ is chlorine and $R_4'$ represent a $C_3$-$C_6$ alkenyl group.

13. The compound according to claim 12, of the formula

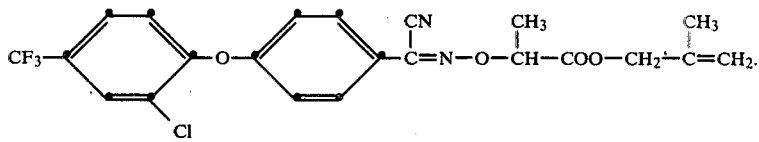

14. A herbicidal composition which contains as active component a herbicidally effective amount of a diphenyl ether oxime derivative of the formula Ia of claim 2, together with carriers and/or other adjuvants.

* * * * *